United States Patent [19]

Aradate et al.

[11] 4,168,436
[45] Sep. 18, 1979

[54] COMPUTED TOMOGRAPHY

[75] Inventors: Hiroshi Aradate, Kawasaki; Tooru Suzuki, Atsugi, both of Japan

[73] Assignee: Tokyo Shibaura Electric Co., Ltd., Japan

[21] Appl. No.: 851,266

[22] Filed: Nov. 14, 1977

[30] Foreign Application Priority Data

Nov. 15, 1976 [JP] Japan .................. 51-136225

[51] Int. Cl.² .................. A61B 6/02; H05G 1/20; H05G 1/22
[52] U.S. Cl. .................. 250/445 T; 250/409; 250/413
[58] Field of Search ........... 250/403, 404, 413, 445 T, 250/409

[56] References Cited

U.S. PATENT DOCUMENTS

| | | | |
|---|---|---|---|
| 2,879,404 | 3/1959 | Rogers et al. | 250/413 |
| 3,069,548 | 12/1962 | Bavor et al. | 250/409 |
| 3,333,104 | 7/1967 | Bougle | 250/409 |
| 4,048,503 | 9/1977 | Taylor | 250/445 T |

Primary Examiner—Alfred E. Smith
Assistant Examiner—T. N. Grigsby
Attorney, Agent, or Firm—Finnegan, Henderson, Farabow & Garrett

[57] ABSTRACT

Computed tomography apparatus having a continuously rotating X-ray projection and detection unit and circuits for controlling the X-ray tube to produce a radiation pulse of predetermined amplitude and duration for each increment of angular motion of the rotating unit. The X-ray tube is controlled by high-voltage switching elements which apply a voltage pulse of precisely measured duration from a charging circuit which supplies a controlled level DC voltage for driving the X-ray tube. A main control circuit responds to position indicating signals from the rotating unit to repetitively operate the charging circuit and the switching elements whereby highly reproducible X-ray pulses irradiate a subject under examination to enable generation of high quality sectional images, i.e., tomograms.

8 Claims, 3 Drawing Figures

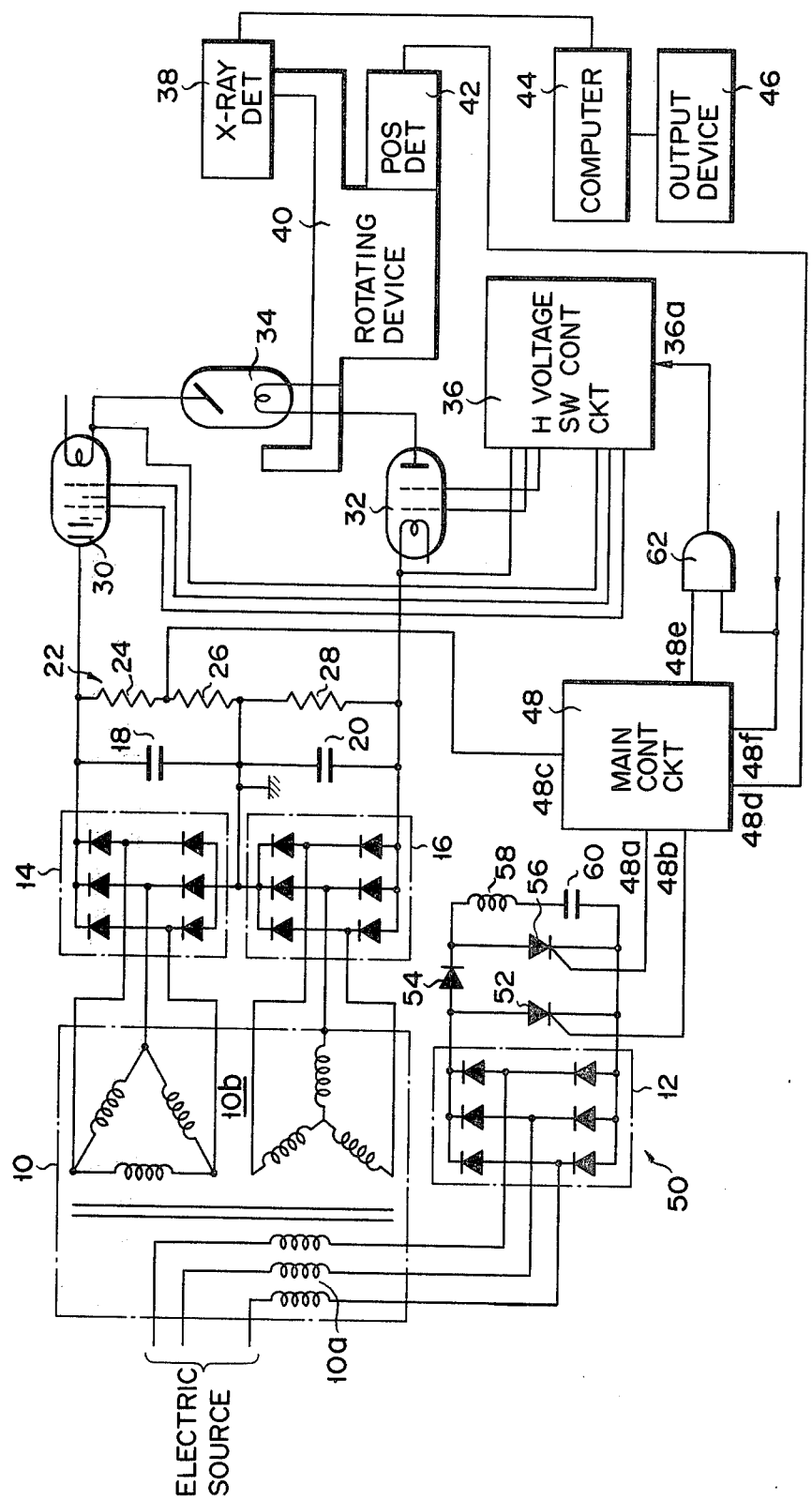
F I G. 1

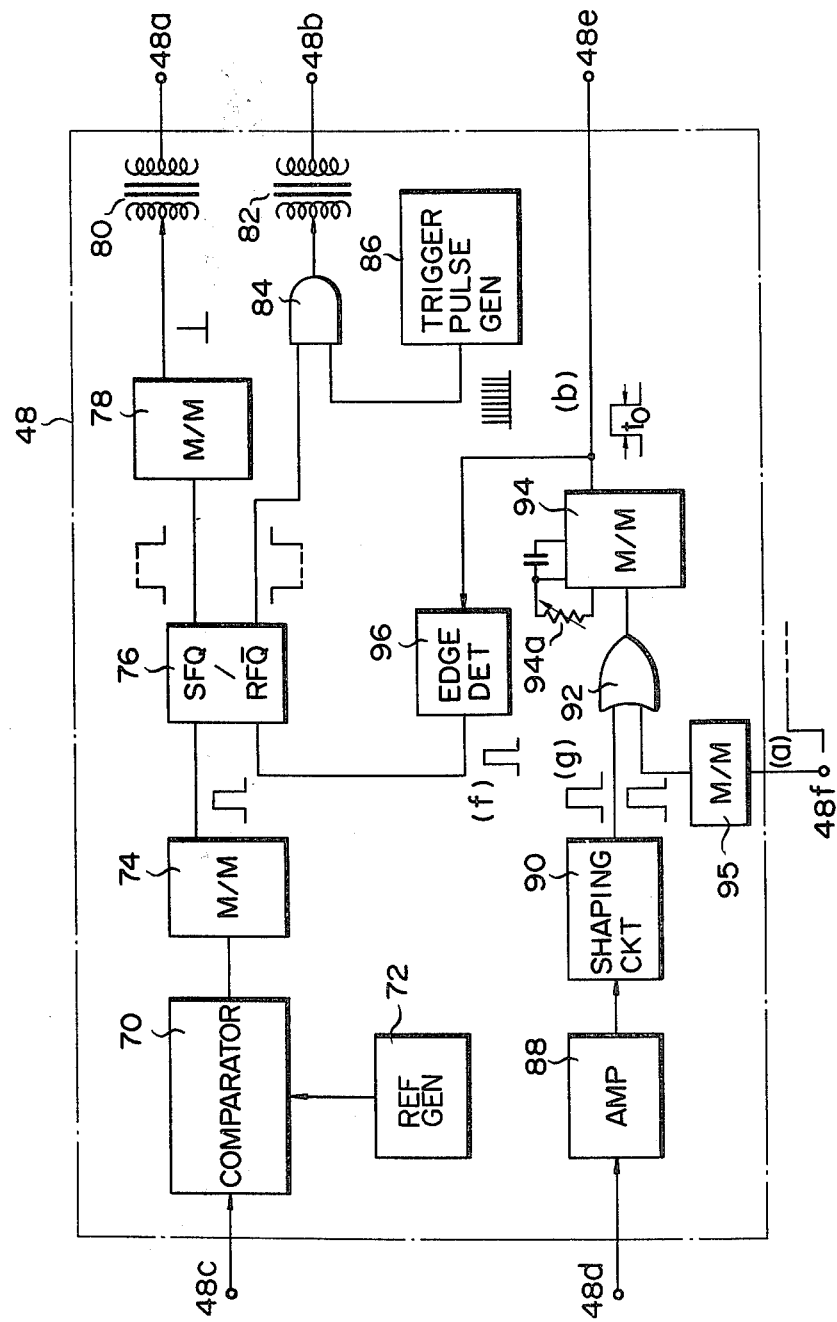

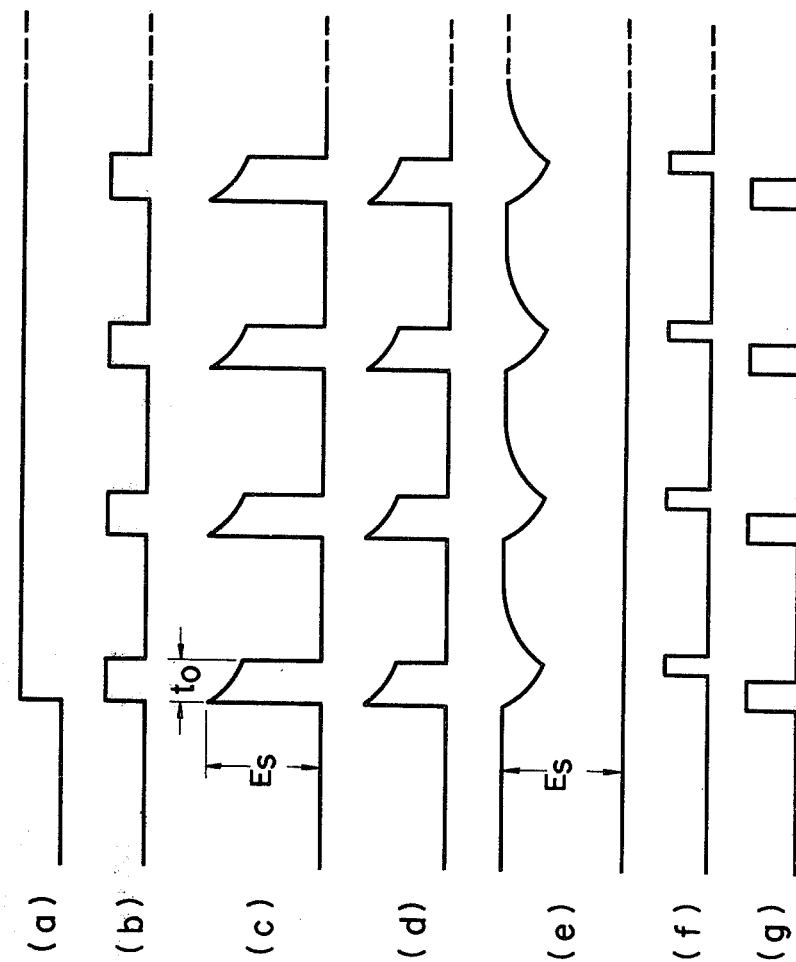

COMPUTED TOMOGRAPHY

This invention relates to a computed tomography to analyze transmission data of X-rays penetrating through a subject by means of a computer and monitor sectional images of the subject.

Nowadays computed tomography equipment is often used in place of conventional tomograph techniques.

In a typical example of a computed tomography system, an X-ray tube and an X-ray detector are disposed facing each other on opposite sides of the subject, and pencil beams or very narrow-spread fan beams of X-rays are emitted from the X-ray tube while the X-ray tube and X-ray detector are scanned rectilinearly through a fixed stroke, exposing the subject to the beams. X-ray transmission data (hereinafter referred to simply as data) is detected at prescribed scan positions (traverse-scanning), and the X-ray tube and X-ray detector are rotated around the axis of the subject body through a prescribed angle. Data is accumulated with every prescribed angular increment of rotation (index-scanning), and then the traverse-scanning is repeated. The data measurements in both trasverse and index scans are repeated as frequently as required. The data transmitted from the X-ray detector is processed by an analog-to-digital converter, applied to the input of a computer for prescribed operational processing, and subjected to computation of the respective X-ray absorption coefficients of suitably divided portions of the subject section, that is, subsections. These X-ray absorption coefficients employed to generate a sectional image of the subject on an output display, such as CRT display or television monitor, and may be printed out at request.

The above method combining traverse and index scanning systems, however, is subject to a defect that the time required for obtaining a single tomogram is as long as 20 seconds to 5 minutes. In order to reduce such inconvenience, there has been devised and put to practical use a second type of system which enables generation of a sectional image in a reduced operating time, approximately 5 seconds. In this second known system, the X-rays emitted from the X-ray tube have the form of a fan beam spreading through an angle covering the whole surface of the objective section of the subject, and the X-ray detector is formed of hundreds of X-ray detecting elements including xenon-enclosed X-ray detectors or semiconductor X-ray detectors, for example, so as to allow simultaneous detection of the data through the whole extent of the fan beam. In this case, the X-rays simultaneously reach a number of X-ray detecting elements, thereby simultaneously providing the data on a number of X-ray transmission paths. Therefore, there is no need for traverse-scanning as is required in the aforesaid conventional example, enabling us to obtain substantially same data by the index-scanning alone.

Generally, in producing a satisfactory tomogram of the subject, especially human body, by using the computed tomography, there are many points to be duly considered. If the time required for the operation is too long, the subject may suffer pain or move, or the internal organs of the subject may move peristaltically or pulsatively, leading to unfavorable results, such as blurred images and excessive exposure. In order to avoid these unfavorable consequences, it is essential first to reduce that data measuring time. Index-scanning should preferably be conducted having a X-ray pulses with smaller duty factor while rotating the X-ray tube and X-ray detector. In this case the amplitude of the X-rays must be a suitable one in compliance with the narrow pulse width of the X-ray pulses, so that the resultant pulses provide a proper dose. The reason of this is that proper data measurement with a good S/N ratio cannot be made unless the dose included in the X-ray pulses exceeds a certain level. If the data measurement is made by means of such X-ray pulses, the data measuring time for a single X-ray pulse will be relatively short, so that index-scanning may be conducted rapidly. In addition, if the X-ray tube and X-ray detector are rotated rapidly, the obtained data will be as stable as is the case with a stationary X-ray tube and X-ray detector. Further, the X-ray pulse, even with a narrow pulse width, are so formed as to include an adequate dose, so that the data may be measured at a satisfactory S/N ratio, controlling the degree of X-ray exposure within a range to secure the safety of the subject under examination and providing sharp sectional images as well as satisfactory measurement data.

In making a number of measurements for the subject section as mentioned above, all the measurements should be made under the same conditions, or else the absorption coefficients for the respective portions of the subject section may be computed incorrectly. The most significant considerations among the above-mentioned requirements are to keep the amplitude, duty factor and waveform of the X-ray pulses constant and to measure the scan direction accurately as well as the correctly use such direction measurement in the operation at the computer.

An object of this invention is to provide a computed tomography apparatus capable of exposing a subject to a highly reproducible X-ray pulse with every rotation of the X-ray tube and X-ray detector through a prescribed angle, thereby index-scanning the subject.

In order to attain the above object, the computed tomography apparatus of the invention is provided with an X-ray tube to project an X-ray beam through a subject; an X-ray detector to produce penetration data in response to X-rays passing through said subject; a scanning means to scan the X-ray beam so as to obtain the penetration data in numerous directions relative to the position of the subject; a position detector for producing signals indicating the direction of the X-ray beam relative to the subject; a computer for executing operations to obtain a tomogram of the subject; an output device for displaying the tomogram in accordance with the results of the computer operations; at least one high-voltage switch connected to the X-ray tube and operable when closed to actuate the X-ray tube to emit X-rays; a DC power source for supplying DC power to the X-ray tube through the high-voltage switch; a main control circuit for controlling the DC power source in response to each signal from the position detector to establish a predetermined voltage level for driving the tube; and a high-voltage switch control circuit operated by the main control circuit for closing the high-voltage switch to actuate the X-ray tube to emit X-rays for a prescribed period of time.

Use of the computed tomography apparatus of the invention as described above will provide various advantages. Since there is used as the energy source to operate the X-ray tube a DC power source and X-ray exposure is conducted by using a true DC voltage, ripple effects normally accompanying rectifying networks are not experienced with the system of the invention. The pattern of X-ray tube voltage drop during X-ray exposure is determined mainly by internal resistance of the X-ray tube, so that high reproducibility may be obtained with every X-ray exposure. Further, the use of the position detector enables highly accurate measurement of the angle of the X-ray tube and X-ray detector. For each X-ray exposure advantages ensure accurate and reliable data on the penetrating X-rays for computation of tomograms, thus providing for generation of far sharper tomograms as compared with those produced by conventional systems. Moreover, in this apparatus, the X-ray exposure is conducted pulsatively, so that the dose of X-rays to which the subject is exposed is substantially reduced as compared with the case of continuous exposure. Additionally, even if the X-ray tube and X-ray detector are rotated rapidly, the effect of such rotation on the measured penetration data may be reduced to a negligible degree by using X-ray pulses with a shorter pulse width, so that the time required for data collection by index-scanning, as well as the time required for obtaining the tomogram of the subject, may be reduced substantially.

This invention can be more fully understood from the following detailed description when taken in conjunction with the accompanying drawings, in which:

FIG. 1 is a schematic circuit diagram showing the overall composition of the computed tomography apparatus of this invention;

FIG. 2 is a block diagram showing the main control circuit shown in FIG. 1; and

FIG. 3 is a timing diagram showing the main pulses and voltages waveforms generated by the circuit of FIG. 2.

FIG. 1 shows the composition and configuration of the computed tomography apparatus of this invention, in which well-known components, as well as a main control circuit as described further in detail with reference to FIG. 2, are each shown in block diagram form.

Referring now to FIG. 1, there are shown a three-phase high-voltage transformer having a primary winding 10a connected to an AC power source, and a secondary winding 10b. The respective neutral side coil ends of the primary winding 10a, which is a three-phase star winding, are connected to the input side of a three-phase rectifier 12. The secondary winding 10b is composed of a delta-connected portion and a star-connected portion, which are connected to the input terminals of three-phase rectifiers 14 and 16 respectively. The negative output terminal of the rectifier 14 and the positive output terminal of the rectifier 16 are grounded, while high-voltage condensers 18 and 20 connected in series are connected between the positive output terminal of the rectifier 14 and the negative output terminal of the rectifier 16. The condenser 18 is connected in parallel with a series circuit composed of bleeder resistances 24 and 26, while the condenser 20 is connected in parallel with a resistance 28. The resistances 24 and 26 form a detection circuit 22 for detecting a voltage proportional to the terminal voltage of the condenser 18. As illustrated, the junctions of the condensers 18 and 20 and of the resistances 26 and 28 are earthed. While the voltage applied to the resistance 26 is proportional to the charging voltage of the condenser 18, it is deemed to be also proportional to the voltage developed across the condensers 18 and 20, i.e., terminal voltage, considering the condenser 20 charged with the same level of voltage as that of the condenser 18. Such proportional voltage is led to a main control circuit 48 as mentioned hereinafter. Numerals 30 and 32 denote tetrodes which function as high-voltage switches. The positive output terminal of the rectifier 14 and the negative output terminal of the rectifier 16 are connected to the anode of the tetrode 30 and the cathode of the tetrode 32 respectively, while the cathode of the tetrode 30 and the anode of the tetrode 32 are connected with the anode and cathode of an X-ray tube 34 respectively. Each tetrode 30 or 32, which is a high-voltage resisting tetrode with first and second grids, is nonconducting with a usually negative voltage impressed between the first grid and cathode, while it is caused to conduct when the negative voltage is converted into a positive voltage. That is, these tetrodes function as switches to make and break the connection between the condensers 18 and 20 and the X-ray tube 34. Each second grid of the tetrodes 30 and 32 is kept at a positive potential against the cathode, as may usually be the case for tetrodes used in this manner.

The first and second grids and cathode of the tetrodes 30 and 32 are connected to a high-voltage switch control circuit 36 for supplying a prescribed voltage. While the control circuit 36 is excluded from the following detailed description because it is well-known, switching of the voltage between the first grid and cathode is effected by a pulse signal supplied to an input terminal 36a of the high-voltage switch control circuit 36. That is, the high-voltage switch control circuit 36 receives the pulse signal and switches the voltage so as to cause the tetrodes 30 and 32 to conduct for a period of time corresponding to the pulse width.

X-rays emitted from the X-ray tube 34, which are pulse-like X-ray fan beams to cover the whole width of a subject section, are projected on an X-ray detector 38 after penetrating through the subject (not shown). X-ray detector 38 provides penetration data for computing the sectional image of the subject. The X-ray tube 34 and X-ray detector 38 are mounted, for example, on a rotating device 40 and measure the penetrated X-rays by means of the pulse-like X-ray fan beams while continuously rotating around the subject. The rotating device 40 is coupled with a well-known position detector, for example, photoelectric rotary encoder 42 available as an angle signal generator, which produces a pulse signal with every rotation of the rotating device 40 through a prescribed angle, e.g., 1°. The signals transmitted from the X-ray detector 38 and rotary encoder 42 are supplied to a computer 44 and subjected to prescribed operational processing, thereby displaying on an output device 46 a sectional image of the subject on the basis of the X-ray absorption coefficient of each portion of the obtained subject section. CRT's, television monitors, etc. may be used for the output device 46. Alternatively, the absorption coefficient of each portion of the section may be typewritten.

The three-phase rectifier 12, which is connected at the input side thereof with the neutral-side coil ends of the primary winding or three-phase star-connected winding of the high-voltage transformer 10 as previously stated, is included in a power switch device 50 to receive signals from a main control circuit 48 and start-stop the boosting operation of the high-voltage transformer 10. The power switch device 50 is provided with the three-phase rectifier 12, a first silicon controlled rectifier (hereinafter referred to as SCR) 52 connected in the forward direction between the output terminals of the rectifier 12, a diode 54 and a second SCR 56 connected in series in the forward direction across the SCR 52, an inductance 58 and a condenser 60 connected in series across the SCR 56. The gate terminals of the SCR's 56 and 52 are connected to terminals 48a and 48b of the main control circuit 48, while the junction of the bleeder resistances 24 and 26 and the output terminal of the rotary encoder 42 are connected to terminals 48c and 48d of the main control circuit 48 respectively. Meanwhile, the main control circuit 48 transmits a pulse signal from a terminal 48e according to the signal from the rotary encoder 42. The main control circuit 48 is further provided with a terminal 48f to receive stepped start signals. Two input terminals of an AND gate 62 are connected to the terminals 48e and 48f of the main control circuit 48 respectively, while its output terminal is connected to a terminal 36a of the high-voltage switch control circuit 36.

Referring now to FIG. 2, there will be described in detail the main control circuit 48. The main control circuit 48 comprises a condenser voltage control circuit, an exposure signal generating circuit and a charging signal generating circuit. The condenser voltage control circuit includes a comparator 70, a reference voltage generator 72, a monostable multivibrator 74, RS flip-flop circuit 76, a monostable multivibrator 78, pulse transformers 80 and 82, an AND gate 84, and a trigger pulse generator 86, while the exposure signal generating circuit includes an amplifier 88, a shaping circuit 90, an OR circuit 92, and monostable multivibrators 94 and 95. The multivibrator 94 is provided with a variable resistance 94a for adjusting the pulse width of the output signal. Further, the charging signal generating circuit includes an edge detector 96.

The comparator 70 is supplied with a voltage proportional to the terminal voltage, i.e., charging voltage of the condensers 18 and 20 connected in series from the terminal 48c by means of the bleeder resistances 24 and 26. This proportional voltage is compared with the reference voltage or set voltage introduced from the reference voltage generator 72 by means of the comparator 70, and when these values are coincident with each other, an output pulse is transmitted from the comparator 70. An output terminal of the comparator 70 is connected to a trigger input terminal of the multivibrator 74, whose output terminal is connected to a set terminal S of the RS flip-flop circuit 76 which is sure to be reset when the power supply is turned on. A first output terminal or reset output terminal $\overline{Q}$ of the flip-flop circuit 76 is connected to one input terminal of the AND gate 84. The other input terminal of the AND gate 84 is connected with an output terminal of the trigger pulse generator 86 to permit the circuit 86 to produce trigger pulses with a high repetition rate, while an output terminal of the AND gate 84 is connected to the gate terminal of the SCR 52 of the power switch device 50 through the pulse transformer 82 and terminal 48b.

Pulse signals transmitted from the rotary encoder 42 by means of the terminal 48d are converted into suitable pulse signals by means of the amplifier 88 and shaping circuit 90 and led to one input terminal of the OR gate 92, the other input terminal of the OR gate 92 being supplied with the output signal of the multivibrator 95 which receives the stepped start signals supplied to the terminal 48f and produces a pulse signal. An output terminal of the OR gate 92 is connected to an input terminal of the multivibrator 94 with the output pulse width determined by the variable resistance 94a. An output terminal of the multivibrator 94 is connected to an input terminal of the edge detector 96. The edge detector 96 receives a pulse signal transmitted from the multivibrator 94 and sends a pulse signal, which rises when the received pulse signal falls, to a reset terminal R of the RS flip-flop circuit 76. A second output terminal or set output terminal Q of the RS flip-flop circuit 76 is connected to an input terminal of the multivibrator 78, whose output power is supplied as trigger pulses to the gate terminal of the SCR 56 used with the power switch device 50 through the pulse transformer 80 and terminal 48a. The output from the multivibrator 94 is connected to terminal 36a of the high-voltage switch control circuit 36 through the terminal 48e and AND gate 62. Where the stepped start signal is supplied to the AND gate 62, the output pulse of the multivibrator 94 with the pulse width set at a desired value $t_O$ by the variable resistance 94a is led to the high-voltage switch control circuit 36, thereby allowing the tetrodes 30 and 32 to conduct for the time $t_O$, so that the X-ray exposure time may be adjusted by controlling the variable resistance 94a.

Referring now to FIGS. 1, 2 and 3, there will be described the operation of the circuits of the invention. First, the reference voltage generator 72 is so adjusted that a signal may be generated by the comparator 70 when the terminal voltage of the condensers 18 and 20 has reached a prescribed level. When the power source is turned on, the output terminal $\overline{Q}$ is activated, because the RS flip-flop circuit 76 is so formed as to be reset. Therefore, immediately on making the power circuit, the AND gate 84 is activated, and an output pulse from the trigger pulse generator 86 is supplied to the gate terminal of the SCR 52 through the AND gate 84, pulse transformer 82, and terminal 48b. When the SCR 52 is allowed to conduct, a neutral point is formed in the primary-side star connection of the high-voltage transformer 10, a high-voltage is produced at the secondary winding 10b and rectified by means of the three-phase rectifiers 14 and 16, and the condensers 18 and 20 are charged. When charging of the condensers 18 and 20 is started, a voltage proportional to the charging voltage or terminal voltage of the condensers 18 and 20 is transmitted from the detection circuit 22 formed of the bleeder resistances 24 and 26 to the terminal 48c of the main control circuit. Such proportional voltage is supplied to the comparator 70, where it is compared with the reference voltage transmitted from the reference voltage generator 72. When these two voltages are coincident with each other, indicating that the terminal voltage of the condensers 18 and 20 has reached a prescribed level, an output signal is transmitted from the comparator 70 and the RS flip-flop circuit 76 is set by the pulse produced by multivibrator 74. An ON signal from the set output terminal Q drives the multivibrator 78, whose output signal is transmitted as a trigger pulse to the gate terminal of the SCR 56 of the power switch device 50, thereby causing the SCR 56 to conduct. Since the condenser 60 is charged by means of the diode 54 by this point of time, when the SCR 56 is allowed to conduct, the condenser 60 discharges to cause a free oscillation in a series resonance circuit including the inductance 58, condenser 60, and SCR 56 of three-phase rectifier 12, and, both SCR's 52 and 56 are converted into the nonconducting state by the initial inverse voltage of the oscillation. In this case the frequency of the free oscillation is set at a very high level, so that both SCR's 52 and 56 are prohibited from conducting immediately after the SCR 56 is allowed to conduct. Accordingly, the neutral point of the primary winding 10a of the high-voltage transformer 10 is opened, charging of the high-voltage condensers 18 and 20 is stopped at the same time, and the terminal voltage of the condensers 18 and 20 is kept at the level set by the reference voltage generator 72 or a prescribed voltage $E_s$.

Meanwhile, when the stepped start signal as shown in FIG. 3(a) is generated, it is converted into a pulse signal by means of the multivibrator 95 and supplied to the multivibrator 94 through the OR gate 92. Further, from the multivibrator 94, there is transmitted a pulse signal with the pulse width of $t_O$ set by the variable resistance 94a as well as with a leading edge synchronized with that of the start signal, as shown in FIG. 3(b). This pulse signal is supplied to the terminal 36a of the high-voltage switch control circuit 36 through the AND gate 62 previously conditioned by receiving the stepped start signal. While a negative voltage is so far applied between the first grid and cathode of the tetrodes 30 and 32 and these tetrodes 30 and 32 are in the nonconducting state, when the terminal 36a is supplied with the pulse signal, the tetrodes 30 and 32 are allowed to conduct for the pulse width $t_O$. Therefore, the electric charges accumulated in the condensers 18 and 20 are discharged through the X-ray tube 34 for a period of $t_O$, and the X-ray tube voltage turns into a pulse voltage with a waveform gradually falling from the prescribed level $E_s$ for a period of $t_O$, as shown in FIG. 3(c). The X-ray tube 34, impressed with the X-ray tube voltage varying in the aforesaid manner, radiates pulse-like X-rays with a waveform similar to that of FIG. 3(c), as shown in FIG. 3(d), for $t_O$. FIG. 3(c) shows the terminal voltage variation of the condensers 18 and 20. Though the terminal voltage $E_s$ may be lowered by the X-ray exposure, it will resume the original level $E_s$ and be kept at the same level, because the condensers 18 and 20 will be automatically charged after completion of the exposure, as described hereinafter. Thereafter, X-ray exposure is conducted with every prescribed angle of rotation correspondingly to the output signal from the rotary encoder 42, as mentioned below. At the time of exposure the X-ray tube voltage waveform varies as shown in FIG. 3(c), the waveform being determined by the voltage $E_s$ as well as by the internal resistances, etc. of the tetrodes 30 and 32 and the X-ray tube 34. As described above, $E_s$ is the terminal voltage of the condensers 18 and 20 automatically determined by setting the reference voltage generator 72, and also the X-ray tube voltage applied to the X-ray tube at the time of the X-ray exposure. Thus, if the detection circuit 22 composed of the bleeder resistances 24 and 26, comparator 70, and reference voltage generator 72 are formed by using materials of good quality and suitable compensating circuits so as to avoid variations due to the environmental conditions and/or external changes, the reproducibility of the level $E_s$ of the terminal voltage will be highly satisfactory. Since the aforesaid X-ray tube current is determined by the internal resistances of the tetrodes 30 and 32 and the X-ray tube 34, which exhibit stable voltage-current characteristics under suitable environmental conditions, the pulse shape of the X-ray tube voltage and hence the variation of the exposure X-ray dose rate with time are substantially constant.

When the X-ray exposure is conducted for a time corresponding to the pulse width $t_O$ of the multivibrator 94, a pulse with a leading edge appearing coincidently with the trailing edge of the output pulse of the multivibrator 94 or at completion of the exposure, as shown in FIG. 3(f), is supplied from the edge detector 96 to the reset input terminal of the RS flip-flop circuit 76. Thus, the RS flip-flop circuit 76 is reset, and the trigger pulse from the trigger pulse generator 86 is supplied to the gate terminal of the SCR 52 by means of the AND gate 84, pulse transformer 82, and terminal 48b, thereby allowing the SCR 52 to conduct. Accordingly, charging of the condensers 18 and 20 is resumed by means of the high-voltage transformer 10. When the terminal voltage of the condensers 18 and 20 reaches the level $E_s$ set by the reference voltage generator 72, the SCR 52 is again rendered nonconducting to stop the charging operation, and the reference voltage $E_s$ is maintained across the condensers 18 and 20, as shown in FIG. 3(e).

As previously stated, when the rotating device 40 rotates through a prescribed angle, e.g., 1°, a pulse signal is transmitted from the rotary encoder 42, converted into the pulse signal as shown in FIG. 3(g) at the main control circuit 48 through the amplifier 88, shaping circuit 90 and OR gate 92, and then supplied to the multivibrator 94. Receiving the aforesaid pulse signal, the multivibrator 94 transmits the pulse with the prescribed pulse width $t_O$ to the high-voltage switch control circuit 36 through the AND gate 62 previously opened by the stepped start signal. In the same manner as the above-mentioned case, the high-voltage switch control circuit 36 allows the tetrodes 30 and 32 to conduct for the time $t_O$, during which pulse-like X-rays are radiated by the X-ray tube 34.

When the X-ray exposure is completed, the RS flip-flop circuit 76 in the main control circuit 48 is reset to allow the SCR 52 to conduct, and the condensers 18 and 20 are charged, thereby raising the terminal voltage of the condensers 18 and 20 once lowered by the X-ray exposure. When the voltage at the condensers 18 and 20 reaches the prescribed voltage $E_s$, charging is stopped and the terminal voltage of the condensers 18 and 20 is maintained at $E_s$, as mentioned above. Therefore, the multivibrator 94 is driven every time the rotary encoder 42 rotates through the prescribed angle to transmit a pulse signal, and there is repeated the same operation as described before.

By employing the electronic circuits of the above embodiment, X-ray pulses are produced with a pulse width of several milliseconds at pulse intervals of some 10 msec. The pulse interval of 10 msec. is a time interval required for disposing a feasible number of detecting elements in the X-ray detector 38, completing the whole scanning within 5 sec. with a feasible number of samples and hence a feasible detection cycles, and obtaining a sharp tomogram required for the diagnosis on the human body.

Although the pulse interval of 10 msec. a pulse width of several milliseconds is given by way of example, various values should be selected in association with the speed of index-scanning without limiting to those values.

Further, by employing the electronic circuits of the invention and setting the source impedance and the capacity of the condensers 18 and 20 at the optimum values to form fully stably the detection circuit 22 for detecting charging voltage (e.g., bleeder resistances 24 and 26) and main control circuit 48, the error in the terminal voltage of the condensers 18 and 20 or X-ray tube voltage applied to the X-ray tube 34 may be reduced to 0.01% or lower, and the reproducibility of the X-ray tube voltage may be increased to as high as 99.99% and above.

According to this invention, as described in connection with the above embodiment, there is provided a computed tomography apparatus which employs X-ray fan beams with a spread to cover the whole width of the subject section and is so formed as to display an image of the section by continuous index-scanning alone, providing various advantages; the X-ray fan beams are pulse-like X-ray fan beams with a substantially constant waveform which are emitted from the X-ray tube according to the pulse-like X-ray tube voltage formed with extremely high reproducibility, so that the data on the penetrating X-rays given by the X-ray detector are highly reliable and the sharpness of the sectional image displayed by the computed tomography apparatus is improved to a degree never attained by conventional apparatus, notwithstanding the substantially reduced display time for the sectional image achieved in accordance with the invention. Further, as X-ray exposure is produced by X-ray pulses of minimum duration, the dose to which the subject is exposed can substantially be reduced as compared with the case of continuous exposure. Further, the errors in the X-ray penetration measurement data due to the angular excursion of the beam during the X-ray exposure are negligible.

Although in the above embodiment the bleeder resistances 24 and 26 are used for detecting the charging voltage of the condensers 18 and 20 connected in series and the condenser 20 is deemed to be charged equally to the condenser 18 by detecting the voltage at the condenser 18, it is to be understood that also available is a system in which the condensers 18 and 20 are provided with separate bleeder resistances for additional accuracy and charging is stopped as soon as the sum of the respective voltages of the condensers 18 and 20 has reached the prescribed level proportional to the prescribed X-ray tube voltage.

Although in the above embodiment start-stop of charging of the condensers 18 and 20 is effected by operating the primary side of the high-voltage transformer 10 by means of the power switch device 50, a high-voltage resisting switching elements, such as tetrodes, may be connected between the secondary winding of the high-voltage transformer 10 and condensers 18 and 20 for improved responsiveness to start-stop, thereby starting and stopping the charging operation with higher responsiveness and closely approximating the terminal voltage of the condensers 18 and 20 after stopping charging to the prescribed level and giving the terminal voltage reproducibility.

Moreover, a potentiometer may, for example, be used in lieu of the rotary encoder 42 for A-D converting the obtained analog signal.

Furthermore, instead of using the tetrodes 30 and 32, triodes with equivalent voltage resisting property may be used or high-voltage resisting semiconductor switching elements may be connected in series so as to obtain the required resisting voltage.

What we claim is:

1. A computed tomography apparatus comprising an X-ray tube to project an X-ray beam through a subject; an X-ray detector to product penetration data in response to X-rays passing through said subject; a scanning means to scan said X-ray beam so as to obtain said penetration data in numerous directions relative to the position of said subject; a position detector for producing signals indicating the direction of said X-ray beam relative to said subject; a computer for executing predetermined operations to obtain a tomogram of said subject; an output device for displaying said tomogram in accordance with the results of said computer operations; at least one high-voltage switch connected to said X-ray tube and operable, when closed, to actuate said tube to emit X-rays; a DC power source for supplying DC power to said X-ray tube through said high-voltage switch; a main control circuit for controlling said DC power source in response to each signal from said position detector to establish a predetermined voltage level for driving said tube; and a high-voltage switch control circuit operated by said main control circuit for closing said high-voltage switch to actuate said X-ray tube to emit X-rays for a prescribed period of time.

2. The computed tomography apparatus according to claim 1, wherein said DC power source includes a high-voltage transformer connected at the input side thereof to an AC power source; recitifer means connected to said high-voltage transformer to supply a DC voltage; condenser means charged by said DC voltage; a detection circuit producing a detection voltage proportional to the terminal voltage of said condensers; and power switch means connected to the input side of said high-voltage transformer and operating in response to actuation of said high-voltage switch control circuit to boost the output thereof to increase said DC voltage.

3. The computed tomography apparatus according to claim 2, wherein said main control circuit includes a condenser voltage control circuit for receiving said detection voltage and deactuating said power switch means when said condensers have been charged to a prescribed level, thereby stopping charging of said condensers, an exposure signal generating circuit for producing an X-ray exposure signal having a prescribed duration in response to each signal received from said position detector, and a charging signal generating circuit for actuating said power switch means with every termination of a signal from said exposure signal generating circuit, thereby recycling said condenser voltage control circuit.

4. The computed tomography apparatus according to claim 3, wherein said condenser voltage control circuit includes a comparator to produce an electric signal when the detection voltage transmitted from said detection circuit has reached a prescribed level; a reference voltage generator to supply said comparator with said prescribed level of voltage; a flip-flop circuit to produce a reset signal in response to termination of said X-ray exposure signal and to produce a set signal in response to said electric signal output from said comparator, said set signal deactuating said power switch means to stop charging of said condensers; a trigger pulse generator for producing continuous trigger pulses; and an AND gate receiving as inputs said trigger pulses and said reset signal from said flip-flop circuit and operating in response thereto to transmit said trigger pulses to actuate said power switch means, thereby allowing said condensers to be charged.

5. The computed tomography apparatus according to claim 4, wherein the primary side of said high-voltage transformer has a three-phase star winding with separated neutral-side coil ends; said power switch means includes a three-phase rectifier connected at the input side thereof with said three neutral-side coil ends, a first silicon controlled rectifier connected in the forward direction to the output side of said rectifier and having the gate terminal thereof connected to the output side of said AND gate in said condenser voltage control circuit, a forward series circuit connected to both sides of said first silicon controlled rectifier and comprising a second silicon controlled rectifier with the gate terminal thereof driven by said set signal from said flip-flop circuit in said condenser voltage control circuit and a diode, and a forward series circuit connected to both sides of said second silicon controlled rectifier and comprising an inductance and a condenser; whereby trigger pulses transmitted from said AND gate drive said first silicon controlled rectifier to operate said three-phase rectifier, thereby forming a neutral point on the primary side of said high-voltage transformer and closing the primary side of said power switch means and said set signal from said flip-flop drives said second silicon controlled rectifier to control said inductance and said condenser to produce an oscillatory signal which arrests the operation of said three-phase recitifer and opens the primary side of said power switch means by releasing the electrical coupling of the neutral point of said three-phase winding.

6. The computed tomography apparatus according to claim 3, wherein said exposure signal generating circuit includes a unistable multivibrator circuit adapted to receive the signal from said position detector and transmit a signal with a prescribed duration to said high-voltage switch control circuit.

7. The computed tomography apparatus according to claim 4, wherein said charging signal generating circuit includes an edge detector to produce a signal with every detection of the trailing edge of an exposure signal from said exposure signal generating circuit, said signal driving the flip-flop circuit in said condenser voltage control circuit to produce said reset signal.

8. The computed tomography apparatus according to claim 1, wherein said high-voltage switch comprises a tetrode.

* * * * *